US00PP27262P3

(12) United States Plant Patent
Suphachadiwong

(10) Patent No.: US PP27,262 P3
(45) Date of Patent: Oct. 11, 2016

(54) *VANDA* PLANT NAMED 'SPCDW1318'

(50) Latin Name: ***Vanda* hybrid**
Varietal Denomination: SPCDW1318

(71) Applicant: Thumrong Suphachadiwong, Chonburi (TH)

(72) Inventor: Thumrong Suphachadiwong, Chonburi (TH)

( * ) Notice: Subject to any disclaimer, the term of this patent is extended or adjusted under 35 U.S.C. 154(b) by 88 days.

(21) Appl. No.: 14/544,030

(22) Filed: Nov. 17, 2014

(65) Prior Publication Data

US 2015/0082501 P1 Mar. 19, 2015

(30) Foreign Application Priority Data

Nov. 19, 2013 (QZ) ..... PBR 2013/2927

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

'SPCDW1318' is a distinctive variety of *Vanda* which is characterized by greyed-red sepal and petal coloration with greyed-purple spots and dark brown floral lip, as well as the stability and uniformity of traits through successive cycles of asexual propagation. The new variety is a *Vanda*, typically produced as an indoor ornamental plant.

3 Drawing Sheets

Latin name of the genus and species: The Latin name of the genus and species of the novel variety disclosed herein is *Vanda* hybrid.

Variety denomination: The inventive variety of *Vanda* disclosed herein has been given the variety denomination 'SPCDW1318'.

BACKGROUND OF THE INVENTION

This application relates to a new cultivar of *Vanda*, as described in EU application number 2013/2927, filed Nov. 19, 2013, grant pending, to which applicant claims priority.

Parentage: The *Vanda* variety 'SPCDW1318' is the result of a planned breeding program. The new variety originated as a seedling from the crossing of the unpatented, proprietary seed parent *Vanda* 'FGN' with the unpatented, proprietary pollen parent referred to as *Vanda* 'NCMN'. The crossing was made by the inventor in his research greenhouse in Chonburi, Thailand in October of 2002.

The new variety was first selected by the inventor, Thumrong Suphachadiwong, a citizen of Thailand, in December of 2007, in a research greenhouse belonging to the inventor in Chonburi, Thailand. After identifying the new variety as a potentially interesting selection, the inventor continued confidential testing and propagation of 'SPCDW1318', assessing stability of the unique characteristics of this variety.

Asexual Reproduction: Asexual reproduction of the new cultivar 'SPCDW1318' was first performed at a commercial laboratory belonging to the inventor in Chonburi, Thailand by tissue culture in January of 2008. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1318' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1318'. These characteristics in combination distinguish 'SPCDW1318' as a new and distinct *Vanda* cultivar:

1. Unique sepal and petal coloration of greyed-red with greyed-purple spots; and,
2. Improved plant compatibility for commercial growing methods; and,
3. Dark brown floral lip.

BOTANICAL DESCRIPTION OF THE PLANT

Figure 1:
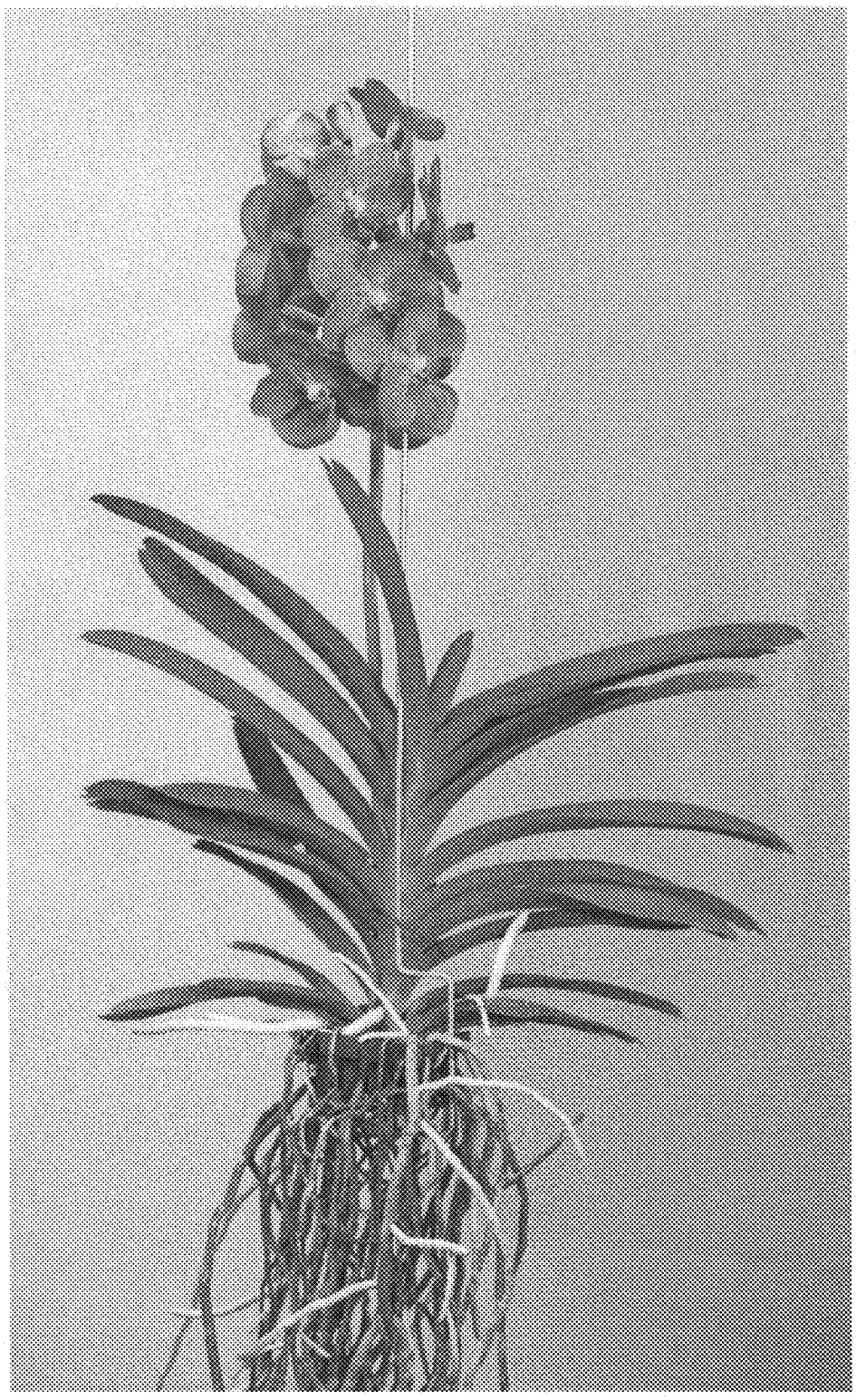
FIG. 1 illustrates, as nearly true as it is reasonably possible to make the same in color photographs of this type, an exemplary plant of 'SPCDW1318' grown in a commercial greenhouse in Honselersdijk, the Netherlands. This plant is approximately 5.5 years old, shown planted in an 8 by 8 cm container.
Figure 2:
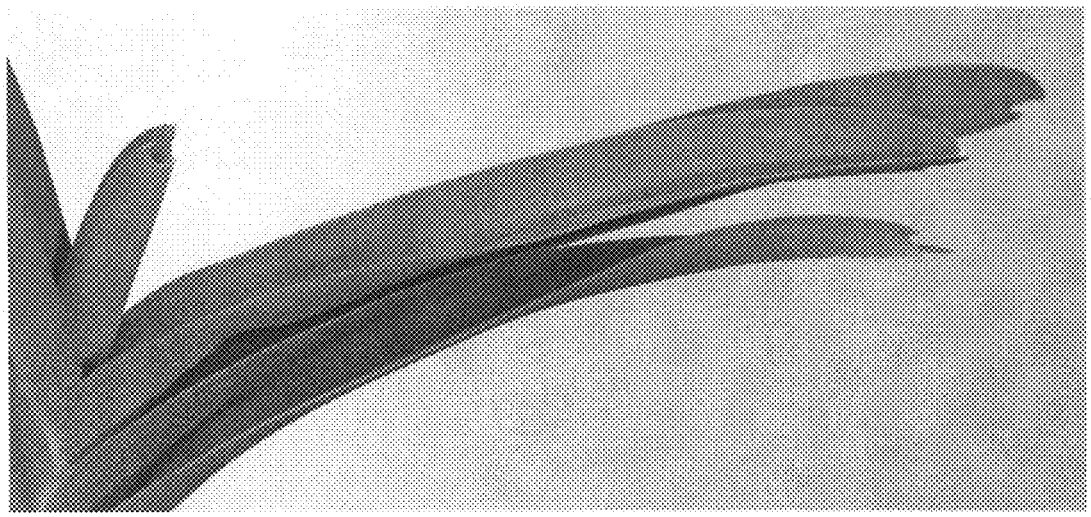
FIG. 2 illustrates, in full color, the typical foliage of 'SPCDW1318'.
Figure 3:
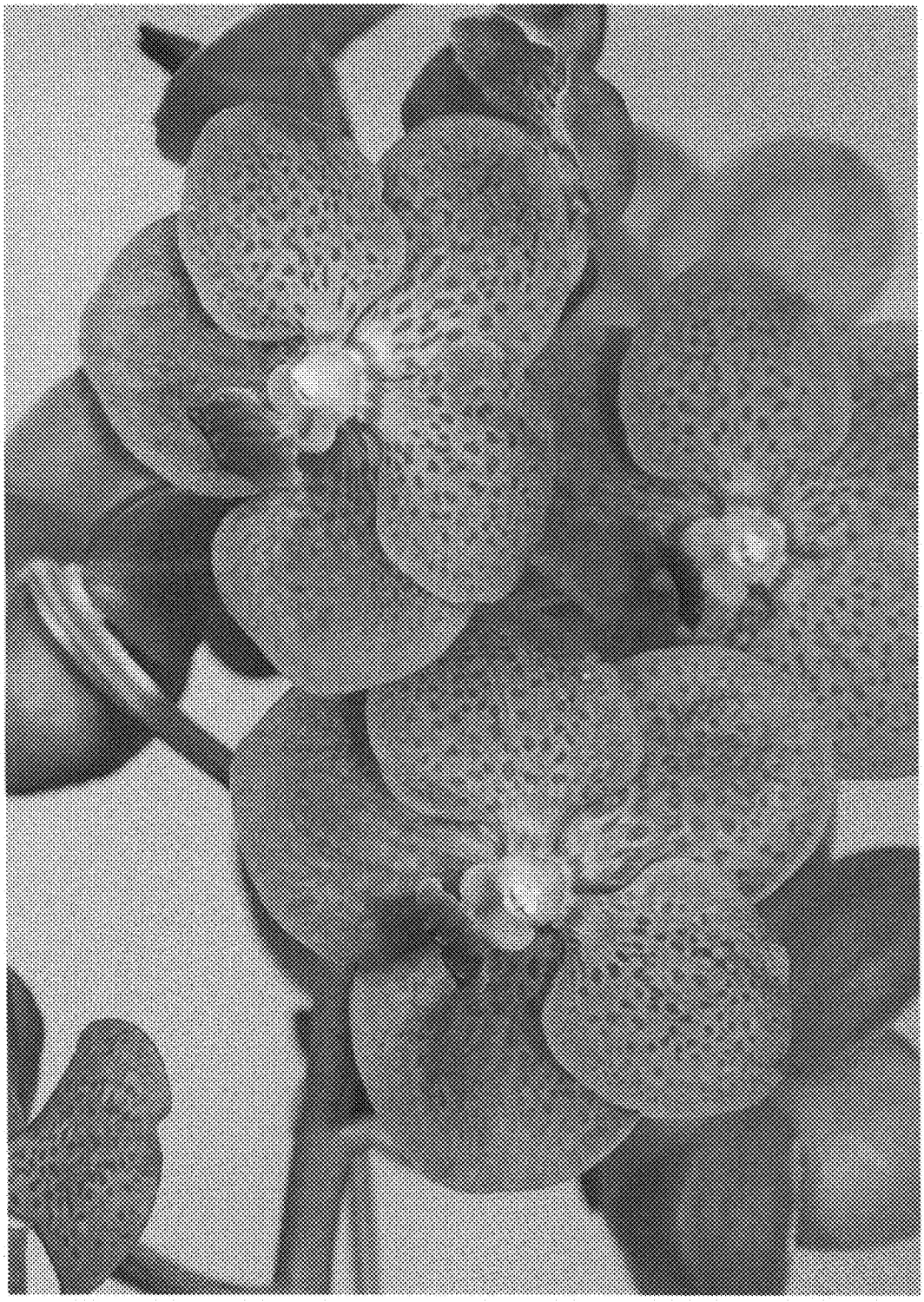
FIG. 3 illustrates, in full color, the typical flowers of 'SPCDW1318'.

The following observations and measurements describe 'SPCDW1318' plants grown in a greenhouse in Honselersdijk, the Netherlands. Temperatures ranged were approximately 23 degrees Celsius during the day and 19 degrees Celsius at night. No photoperiodic or chemical treatments were given to the plants. When natural lighting fell below 150 Watt, artificial lighting is given at 10,000 lux for 16 hours a day. Measurements and numerical values represent averages of typical plant types.

Those skilled in the art will appreciate that certain characteristics will vary with older or, conversely, with younger plants. 'SPCDW1318' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

A botanical description of 'SPCDW1318' and comparisons with other varieties of *Vanda* are provided below.

TECHNICAL DESCRIPTION OF THE VARIETY

Plant description:

*Growth habit*.—Monopodial, upright.

*Average height from base (plant grown in hanging basket, so no soil line present) to top of foliage*.—38.0 cm.

*Average height from base (plant grown in hanging basket, so no soil line present) to top of flowers*.—60.0 cm.

*Plant spread*.—Average of 36.8 cm.

*Normal pot size*.—Hanging basket (8 by 8 cm square).

*Growth rate*.—Moderate.

*Number of leaves per plant*.—Average of 21.

*Propagation type*.—Tissue Culture.

*Propagation details*.—The time needed from for the start of a mericlone to get the small plants ready for deflasking is approximately 24 months under a controlled temperature of about 26 degrees Celsius. After that period plants have matured roots. Plants start to make roots in the last 6 months in flasks. After deflasking they remain in a shaded and controlled environment.

*Disease resistance*.—Good resistance to the normal diseases found in *Vanda*.

*Drought tolerance and cold tolerance*.—Drought tolerance is typical for species. Superior cold tolerance, to approximately 6 degrees Celsius.

Root system: Moderately to heavy rooting with aerial roots only. Roots very fleshy, non-fibrous. Average length of old roots is 55.1 cm, average diameter of old roots is 0.4 cm, average diameter of young roots is 0.7 cm. Old roots colored yellow-green; near RHS 146D. Young roots colored greyed-green; near RHS 192C to 192D, growing tips of roots yellow-green; 152A.

Foliage:

*Arrangement*.—Distichous.

*Average length*.—Approximately 26.0 cm.

*Average width*.—Approximately 2.8 cm.

*Shape of blade*.—Ligulate, strongly carinate.

*Aspect*.—Moderately curved.

*Apex*.—Unequal to unequal emarginated.

*Base*.—Sheathing.

*Sheath length*.—Average 1.9 cm.

*Sheath width*.—Average 1.6 cm.

*Sheath color*.—Green; near RHS N144D.

*Margin*.—Entire.

*Texture of top surface*.—Glabrous, very slightly glossy.

*Texture of bottom surface*.—Glabrous, matte.

*Color of young foliage, upper side*.—Yellow-green; near RHS 144A.

*Color of young foliage, under side*.—Yellow-green to green; in between near RHS 143B and 144A.

*Color of mature foliage, upper side*.—Green; near RHS 137B.

*Color of mature foliage, under side*.—Yellow-green; near RHS 146B.

*Venation*.—Parallel.

*Venation coloration*.—As leaf surface; upper side green; near RHS 137B and lower side yellow-green; near RHS 146B.

*Petiole*.—No petioles present, leaves sessile.

Inflorescence:

*Flowers per stem*.—Average of 13.

*Inflorescence arrangement*.—Axially placed raceme.

*Inflorescence height*.—Approximately 22.4 cm (measured from base of lowest flower to top of upper flower).

*Inflorescence width*.—Approximately 14.7 cm.

*Peduncle*.—Length — Approximately 45.0 cm. Width — Approximately 0.8 cm. Aspect — Approximately 20° angle to rosette. Strength — Strong. Texture — Smooth, moderately glossy. Color — Yellow-green; near RHS 144A.

Bud:

*Rate of opening*.—Buds open approximately three weeks from first sight.

*Length*.—Average of 1.7 cm.

*Diameter*.—Average of 1.6 cm.

*Shape*.—Broad obovate.

*Color*.—Greyed-red; near RHS 178A but slightly darker, base yellow-green; near RHS 150C.

Flower:

*Flower type*.—Zygomorphic (orchidaceous), typical shape for the genus *Vanda*.

*Shape*.—Zygomorphic, consisting of three sepals and three petals, one of which is transformed into a labellum (lip).

*Length (height)*.—Approximately 8.5 cm.

*Width*.—Approximately 8.5 cm.

*Depth*.—Approximately 2.8 cm.

*Fragrance*.—No fragrance.

*Lastingness*.—6 to 8 weeks, depending on growing conditions.

*Persistent*.—No.

*Quantity of petals*.—3 (2 "traditional" petals and a labellum (lip), described separately).

*Petals*.—Arrangement — one lateral petal on each side. Length — Approximately 3.9 cm. Width — Approximately 3.8 cm. Shape — Near orbicular to broad ovate. Apex — Obtuse. Base — Cuneate. Margin — Entire, very slightly undulate. Texture of Upper forward surface — Glabrous, matte, velvety. Texture of Lower back surface — Glabrous, matte, velvety. Color When opening, forward surface — Yellow; near RHS 11B, finely dotted greyed-red; near RHS 182C and 182D. Petal heavily dotted with larger dots, greyed-purple; near RHS 183B and 183C. Color When opening, back surface — Yellow; near RHS 11B and 11C, tinged greyed-red towards the margins and top; near RHS 182A and 182B. Color When Fully Opened, forward surface — Greyed-red; near RHS 178B, heavily dotted; greyed-purple; near RHS 183A and 183B. Color When Fully Opened, back surface — Greyed-red; near RHS 178B and 178C, base greyed-orange; near RHS 164C. Fading, forward surface — Not fading. Fading, back surface — Not fading. Color Venation Fully Opened, forward surface — Veins not visible, colored as petal surface. Color Venation Fully Opened, back surface — Main vein greyed-orange; near RHS 164B, other veins as petal surface. Labellum/Lip: Shape — Three-lobed, lateral lobes involute, central lobe very slightly revolute. Length — Approximately 1.8 cm (excl. spur). Width — Approximately 1.7 cm. Texture — Glabrous, slightly glossy, with 3 callosities. Apex — Emarginate to straight. Base — Cuneate. Color When Opening, forward surface — Lateral lobes yellow and yellow-orange; near RHS 9B and 15A. Central lobe and callosities greyed-purple; in between near RHS 183A and 185A, base greyed-orange; near RHS 176D. Color When Opening, back surface — Lateral lobes yellow; near RHS 8B. Central lobe greyed-purple; in between near RHS 183A and 185A, base greyed-orange; near RHS 176B. Color When Fully Opened, forward surface — Lateral lobes yellow and yellow-orange; near RHS 13A and 21A. Central lobe and callosities greyed-purple; near RHS 183A but darker, base greyed-orange; near RHS 176B to 176C. Color When Fully Opened, back surface — Lateral lobes yellow; near RHS 9B and 12B. Central lobe greyed-purple; near RHS 183A but darker, margins greyed-orange; near RHS 174A, base lighter; near RHS 164B. Fading, forward surface — Not fading. Fading, back surface — Not fading. Color Venation Fully Opened, forward surface — No venation visible on labellum. Color Venation Fully Opened, back surface — No venation visible on labellum. Margin — Entire.

*Spurs*.—Quantity — Average of 1. Appearance — Short triangular, in line with central lobe of labellum. Length — Approximately 0.8 cm. Width — Approximately 0.55 cm. Height — Approximately 0.6 cm (at the base). Shape — Short triangular. Apex — Obtuse. Base — Broad cuneate. Margin — Entire. Texture — Glabrous, very slightly glossy. Color — Yellow-orange; near RHS 20B.

*Sepals*.—Quantity — Average of 3. Appearance — One dorsal sepal (pointing upright) and two lateral sepals. Length — Dorsal sepal approximately 4.5 cm and lateral sepals approximately 4.2 cm. Width — Dorsal sepal approximately 4.0 cm and lateral sepals approximately 4.4 cm. Shape — Dorsal sepal broad ovate to near orbicular. Lateral sepals near orbicular to reniform. Apex — Obtuse. Base — Cuneate. Margin — Entire. Texture — Glabrous, matte, velvety. Color — Dorsal sepal greyed-red; near RHS 178B, lighter towards the margins; near 178C and 178D, base greyed-orange; near 164B, heavily dotted greyed-purple; near RHS 183B. Lateral sepals greyed-red; near RHS 178A, heavily dotted greyed-purple; near RHS 183A and 183B.

*Pedicels*.—Length — Approximately 5.9 cm. Diameter — Approximately 0.6 cm. Angle — Approximately 80° angle to peduncle. Strength — Very strong. Texture — Glabrous, axially angled with 5 "ribs", axially twisted (due to resupination), glossy. Color — Greyed-purple; near RHS 185D.

Reproductive organs:

*Stamens, style and stigma fused into column?*.—Yes. Column Length — Approximately 0.7 cm. Column Diameter — Approximately 0.7 cm. Column Color — Yellow; near RHS 12B, under side lighter; 7B. Ovary Position — Inferior. Ovary Diameter — Approximately 0.5 cm. Ovary Color — Yellow; near RHS 8A. Pollen Color — Yellow; near RHS 13A.

Seed and fruit: Seed production has not been observed.

Comparisons with parent plants: Plants of the new cultivar 'SPCDW1318' are similar to the seed parent, *Vanda* 'FGN' in most horticultural characteristics. The new variety, however, exhibits greyed-red flowers with greyed-red spots, whereas the seed parent exhibits yellow flowers. Plants of the new cultivar 'SPCDW1318' are similar to the pollen parent, *Vanda* 'NCMN' in most horticultural characteristics. Plants of the new variety, however, are larger, with a longer leaf span than the pollen parent.

Comparisons with other commercial *Vanda*: 'SPCDW1318' is similar in most horticultural characteristics to the commercial variety *Vanda* 'Blue Magic' (not patented). The new variety, however, produces sepals and petals colored orange-brown with brown spots whereas 'Blue Magic' produces petals and sepals that are white with thick, dark purple netting. The new variety has smaller flowers than 'Blue Magic'.

That which is claimed is:

1. A new and distinct variety of *Vanda* plant named 'SPCDW1318', substantially as described and illustrated herein.

* * * * *